United States Patent

Osadchy et al.

(10) Patent No.: US 12,059,535 B2
(45) Date of Patent: Aug. 13, 2024

(54) MANAGING MEDICAL DEVICE EQUIPMENT BY ONLINE MAGNETIC CALIBRATION OF A CATHETER

(71) Applicant: Biosense Webster (Israel) Ltd., Yokneam (IL)

(72) Inventors: Daniel Osadchy, Haifa (IL); Meir Bar-Tal, Haifa (IL); Avram Dan Montag, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 858 days.

(21) Appl. No.: 17/161,015

(22) Filed: Jan. 28, 2021

(65) Prior Publication Data

US 2022/0233818 A1 Jul. 28, 2022

(51) Int. Cl.
*A61M 25/01* (2006.01)
*G16H 40/40* (2018.01)
*G16H 40/63* (2018.01)
*A61B 18/00* (2006.01)
*A61B 18/14* (2006.01)

(52) U.S. Cl.
CPC ........ *A61M 25/0105* (2013.01); *G16H 40/40* (2018.01); *G16H 40/63* (2018.01); *A61B 2018/00577* (2013.01); *A61B 18/1492* (2013.01); *A61M 2025/0166* (2013.01); *A61M 2205/702* (2013.01)

(58) Field of Classification Search
CPC ....... A61B 5/283; A61B 5/367; A61B 5/6852; A61B 2560/0223; A61B 2018/00577; A61B 18/1492; A61M 25/0105; A61M 2205/0166; A61M 2205/702; G16H 40/40; G16H 40/63
USPC ........................................................ 702/104
See application file for complete search history.

(56) References Cited

U.S. PATENT DOCUMENTS

| 6,484,118 | B1 | 11/2002 | Govari |
| 7,809,421 | B1 | 10/2010 | Govari |
| 8,792,962 | B2 | 7/2014 | Esguerra et al. |
| 2010/0331644 | A1* | 12/2010 | Neale ................... A61N 1/05 600/345 |
| 2014/0188422 | A1 | 7/2014 | Huber et al. |
| 2019/0328274 | A1 | 10/2019 | Gliner et al. |
| 2020/0046250 | A1 | 2/2020 | Govari |

FOREIGN PATENT DOCUMENTS

EP 1585434 B1 10/2005

OTHER PUBLICATIONS

Extended European Search Report dated Jun. 22, 2022 for European Patent Application No. 22153592.5.

* cited by examiner

*Primary Examiner* — John H Le
(74) *Attorney, Agent, or Firm* — Volpe Koenig (57) ABSTRACT

A method for calibrating a medical device is provided. The method implemented by a calibration engine executed by one or more processors. The method includes capturing one or more voltage measurements by one or more components of a catheter, estimating calibration data based on the one or more voltage measurements, and outputting the calibration data to the catheter.

20 Claims, 5 Drawing Sheets

CHART 500

| POINTS | MEASUREMENTS | LOCATION PARAMETERS | CALIBRATION PARAMETERS |
|---|---|---|---|
| 1 | 27 | 6 | 6 |
| 10 | 270 | 60 | 6 |
| 100 | 2700 | 600 | 6 |

FIG. 5

MANAGING MEDICAL DEVICE EQUIPMENT BY ONLINE MAGNETIC CALIBRATION OF A CATHETER

FIELD OF INVENTION

The present invention is related to medical device equipment. More particularly, the present invention relates to managing medical device equipment by online magnetic calibration of a catheter.

BACKGROUND

Currently, as a part of a manufacturing process, a catheter is calibrated to accurately visualize and navigate inside a body of a patient. During the calibration, the catheter is placed in a middle of a calibration chamber so that three orthogonal fields are applied. Sensors of the catheter take voltage measurements, and orientation and sensitivity of each sensor is determined based on the applied three orthogonal fields. The orientation and sensitivity is stored in a memory of the catheter (e.g., a read/write memory component, such as an EEPROM). Presently, there are no techniques that calibrate the catheter on-site or in-the-field without employing, locally, expensive and bulky calibration chambers. Also, due to the lack of techniques, a catheter aging problem (e.g., calibration parameter changes over time) also remains unaddressed.

SUMMARY

According to an exemplary embodiment, a method is provided. The method implemented by a calibration engine executed by one or more processors. The method includes capturing one or more voltage measurements by one or more components of a catheter, estimating calibration data based on the one or more voltage measurements, and outputting the calibration data to the catheter.

According to one or more embodiments, the exemplary method embodiment above can be implemented as an apparatus, a system, and/or a computer program product.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

Disclosed herein is a system and method that relates to managing medical device equipment by online magnetic calibration of a catheter. The system and method can be implemented as an online magnetic calibration system driven by a calibration engine. In this way, the calibration engine and the online magnetic calibration system particularly utilizes and transforms medical device equipment to enable/implement the online magnetic calibration of the catheter that are otherwise not currently available or currently performed by cardiac physicians and medical personnel. The calibration engine can a processor executable code or software that is necessarily rooted in process operations by, and in processing hardware of, medical device equipment (e.g., the online magnetic calibration system). For ease of explanation, the calibration engine is described herein with respect to mapping a heart; however, any anatomical structure, body part, organ, or portion thereof can be a target for mapping when operating the calibration engine described herein.

One or more advantages, technical effects, and/or benefits of the calibration engine and the online magnetic calibration system include addressing a need for on-site or in-the-field catheter calibration by producing an automatic calibration during navigation of the catheter within a patient. Note that the term "online" refers to the ability to calibrate during the actual procedure. Note that the term "automatic calibration" refers to the ability to adjust catheter sensitivity and/or direction during the actual procedure. Further, the calibration engine and the online magnetic calibration system eliminates a need for local calibration chambers and obviates the catheter aging problem, as the catheter is used immediately after calibration (e.g., and not several months or years after). Furthermore, the calibration engine and the online magnetic calibration system can be adapted and implemented into existing surgical/mapping systems and work with any catheter.

Figure 1:
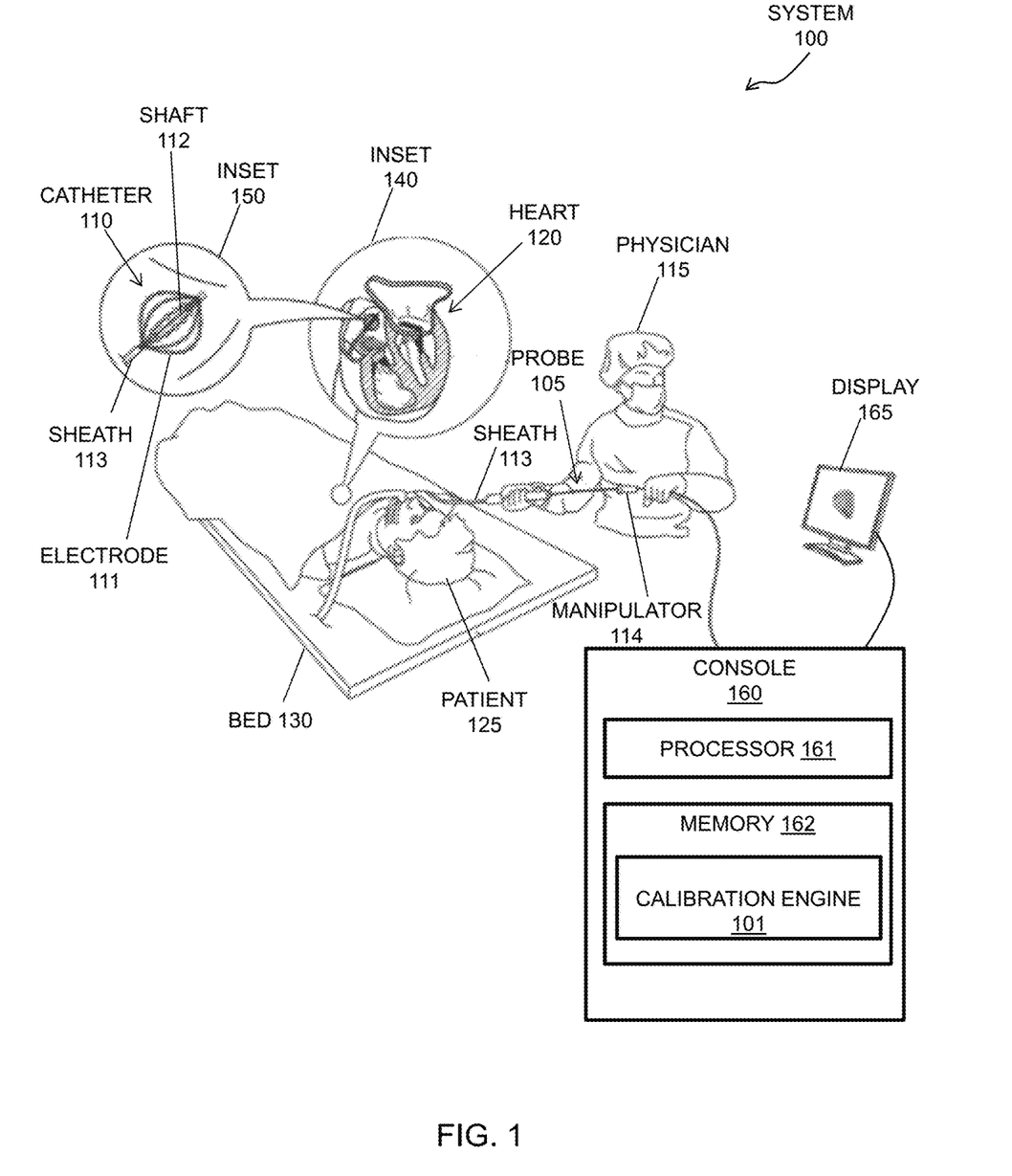
FIG. 1 illustrates a diagram of an exemplary system in which one or more features of the disclosure subject matter can be implemented according to one or more embodiments.

FIG. 1 is a diagram of an example system (e.g., medical device equipment), shown as a system 100, in which one or more features of the subject matter herein can be implemented according to one or more embodiments. All or part of the system 100 can be used to collect information (e.g., biometric data and/or a training dataset) and/or used to implement a calibration engine 101 as described herein. The system 100, as illustrated, includes a probe 105 with a catheter 110 (including at least one electrode 111), a shaft 112, a sheath 113, and a manipulator 114. The system 100, as illustrated, also includes a physician 115 (or a medical professional or clinician), a heart 120, a patient 125, and a bed 130 (or a table). Note that insets 140 and 150 show the heart 120 and the catheter 110 in greater detail. The system 100 also, as illustrated, includes a console 160 (including one or more processors 161 and memories 162) and a display 165. Note further each element and/or item of the system 100 is representative of one or more of that element and/or that item. The example of the system 100 shown in FIG. 1 can be modified to implement the embodiments disclosed herein. The disclosed embodiments can similarly be applied using other system components and settings. Additionally, the system 100 can include additional components, such as elements for sensing electrical activity, wired or wireless connectors, processing and display devices, or the like.

The system 100 can be utilized to detect, diagnose, and/or treat cardiac conditions (e.g., using the calibration engine 101). Cardiac conditions, such as cardiac arrhythmias, persist as common and dangerous medical ailments, especially in the aging population. For instance, the system 100 can be part of a surgical system (e.g., CARTO® system sold by Biosense Webster) that is configured to obtain biometric data (e.g., anatomical and electrical measurements of a patient's organ, such as the heart 120) and perform a cardiac ablation procedure. More particularly, treatments for cardiac conditions such as cardiac arrhythmia often require obtaining a detailed mapping of cardiac tissue, chambers, veins, arteries and/or electrical pathways. For example, a prerequisite for performing a catheter ablation (as described herein) successfully is that the cause of the cardiac arrhythmia is accurately located in a chamber of the heart 120. Such locating may be done via an electrophysiological investigation during which electrical potentials are detected spatially resolved with a mapping catheter (e.g., the catheter 110) introduced into the chamber of the heart 120. This electrophysiological investigation, the so-called electro-anatomical mapping, thus provides 3D mapping data which can be displayed on a monitor. In many cases, the mapping function and a treatment function (e.g., ablation) are provided by a single catheter or group of catheters such that the mapping catheter also operates as a treatment (e.g., ablation) catheter at the same time. In this case, the calibration engine 101 can be directly stored and executed by the catheter 110, as an online magnetic calibration algorithm.

In patients (e.g., the patient 125) with normal sinus rhythm (NSR), the heart (e.g., the heart 120), which includes atrial, ventricular, and excitatory conduction tissue, is electrically excited to beat in a synchronous, patterned fashion. Note that this electrical excitement can be detected as intracardiac electrocardiogram (IC ECG) data or the like.

In patients (e.g., the patient 125) with a cardiac arrhythmia (e.g., atrial fibrillation or aFib), abnormal regions of cardiac tissue do not follow a synchronous beating cycle associated with normally conductive tissue, which is in contrast to patients with NSR. Instead, the abnormal regions of cardiac tissue aberrantly conduct to adjacent tissue, thereby disrupting the cardiac cycle into an asynchronous cardiac rhythm. Note that this asynchronous cardiac rhythm can also be detected as the IC ECG data. Such abnormal conduction has been previously known to occur at various regions of the heart 120, for example, in the region of the sino-atrial (SA) node, along the conduction pathways of the atrioventricular (AV) node, or in the cardiac muscle tissue forming the walls of the ventricular and atrial cardiac chambers. There are other conditions, such as flutter, where the pattern of abnormally conducting tissues lead to reentry paths such that the chamber beats in a regular pattern that can be multiple times the sinus rhythm.

In support of the system 100 detecting, diagnosing, and/or treating cardiac conditions, the probe 105 can be navigated by the physician 115 into the heart 120 of the patient 125 lying on the bed 130. For instance, the physician 115 can insert the shaft 112 through the sheath 113, while manipulating a distal end of the shaft 112 using the manipulator 114 near the proximal end of the catheter 110 and/or deflection from the sheath 113. As shown in an inset 140, the catheter 110 can be fitted at the distal end of the shaft 112. The catheter 110 can be inserted through the sheath 113 in a collapsed state and can be then expanded within the heart 120.

Generally, electrical activity at a point in the heart 120 may be typically measured by advancing the catheter 110 containing an electrical sensor at or near its distal tip (e.g., the at least one electrode 111) to that point in the heart 120, contacting the tissue with the sensor and acquiring data at that point. One drawback with mapping a cardiac chamber using a catheter type containing only a single, distal tip electrode is the long period of time required to accumulate data on a point-by-point basis over the requisite number of points required for a detailed map of the chamber as a whole. Accordingly, multiple-electrode catheters (e.g., the catheter 110) have been developed to simultaneously measure electrical activity at multiple points in the heart chamber.

The catheter 110, which can include the at least one electrode 111 and a catheter needle coupled onto a body thereof, can be configured to obtain biometric data, such as electrical signals of an intra-body organ (e.g., the heart 120), and/or to ablate tissue areas of thereof (e.g., a cardiac chamber of the heart 120). Note that the electrodes 111 are representative of any like elements or components, such as tracking coils, piezoelectric transducer, electrodes, axial sensors, or combination of elements configured to ablate the tissue areas or to obtain the biometric data. According to one or more embodiments, the catheter 110 can include one or more position sensors that used are to determine trajectory information. The trajectory information can be used to infer motion characteristics, such as the contractility of the tissue.

Biometric data (e.g., patient biometrics, patient data, or patient biometric data) can include one or more of local activation times (LATs), electrical activity, topology, bipolar mapping, reference activity, ventricle activity, dominant frequency, impedance, or the like. The LAT can be a point in time of a threshold activity corresponding to a local activation, calculated based on a normalized initial starting point. Electrical activity can be any applicable electrical signals that can be measured based on one or more thresholds and can be sensed and/or augmented based on signal to noise ratios and/or other filters. A topology can correspond to the physical structure of a body part or a portion of a body part and can correspond to changes in the physical structure relative to different parts of the body part or relative to different body parts. A dominant frequency can be a frequency or a range of frequency that is prevalent at a portion of a body part and can be different in different portions of the same body part. For example, the dominant frequency of a PV of a heart can be different than the dominant frequency of the right atrium of the same heart. Impedance can be the resistance measurement at a given area of a body part.

Examples of biometric data include, but are not limited to, patient identification data, IC ECG data, bipolar intracardiac reference signals, anatomical and electrical measurements, trajectory information, body surface (BS) ECG data, historical data, brain biometrics, blood pressure data, ultrasound signals, radio signals, audio signals, a two- or three-dimensional image data, blood glucose data, and temperature data. The biometrics data can be used, generally, to monitor, diagnosis, and treatment any number of various diseases, such as cardiovascular diseases (e.g., arrhythmias, cardiomyopathy, and coronary artery disease) and autoimmune diseases (e.g., type I and type II diabetes). Note that BS ECG data can include data and signals collected from electrodes on a surface of a patient, IC ECG data can include data and signals collected from electrodes within the patient, and ablation data can include data and signals collected from tissue that has been ablated. Further, BS ECG data, IC ECG data, and ablation data, along with catheter electrode position data, can be derived from one or more procedure recordings.

For example, the catheter 110 can use the electrodes 111 to implement intravascular ultrasound and/or MRI catheterization to image the heart 120 (e.g., obtain and process the biometric data). Inset 150 shows the catheter 110 in an enlarged view, inside a cardiac chamber of the heart 120. Although the catheter 110 is shown to be a point catheter, it will be understood that any shape that includes one or more electrodes 111 can be used to implement the exemplary embodiments disclosed herein.

Examples of the catheter 110 include, but are not limited to, a linear catheter with multiple electrodes, a balloon catheter including electrodes dispersed on multiple spines that shape the balloon, a lasso or loop catheter with multiple electrodes, or any other applicable shape. Linear catheters can be fully or partially elastic such that it can twist, bend, and or otherwise change its shape based on received signal and/or based on application of an external force (e.g., cardiac tissue) on the linear catheter. The balloon catheter can be designed such that when deployed into a patient's body, its electrodes can be held in intimate contact against an endocardial surface. As an example, a balloon catheter can be inserted into a lumen, such as a pulmonary vein (PV). The balloon catheter can be inserted into the PV in a deflated state, such that the balloon catheter does not occupy its maximum volume while being inserted into the PV. The balloon catheter can expand while inside the PV, such that those electrodes on the balloon catheter are in contact with an entire circular section of the PV. Such contact with an entire circular section of the PV, or any other lumen, can enable efficient imaging and/or ablation.

According to other examples, body patches and/or BS electrodes, or one or more other transmitters, may also be positioned on or proximate to a body of the patient 125. The catheter 110 with the one or more electrodes 111 can be positioned within the body (e.g., within the heart 120) and a position of the catheter 110 can be determined by the 100 system based on signals transmitted and received between the one or more electrodes 111 of the catheter 110 and the body patches and/or BS electrodes (e.g., the transmitters). For instance, one or more transmitters (e.g., 9 transmitters) can be positioned externally to the patient 125, such as under the bed 130, and provide a magnetic field that induces one or more voltage measurements for detection in the one or more components by the catheter 110. Additionally, the electrodes 111 can sense the biometric data from within the body of the patient 125, such as within the heart 120 (e.g., the electrodes 111 sense the electrical potential of the tissue in real time). The biometric data can be associated with the determined position of the catheter 110 such that a rendering of the patient's body part (e.g., the heart 120) can be displayed and show the biometric data overlaid on a shape of the body part.

The probe 105 and other items of the system 100 can be connected to the console 160. The console 160 can include any computing device, which employs the online magnetic calibration algorithm (which can be included in and/or represented as the calibration engine 101). According to an exemplary embodiment, the console 160 includes the one or more processors 161 (any computing hardware) and the memory 162 (any non-transitory tangible media), where the one or more processors 161 execute computer instructions with respect the calibration engine 101 and the memory 162 stores these instructions for execution by the one or more processors 161. For instance, the console 160 can be configured to receive and process the biometric data and determine if a given tissue area conducts electricity. In some embodiments, the console 160 can be further programmed by the calibration engine 101 (in software) to carry out the functions of capturing one or more voltage measurements by one or more components of a catheter, estimating calibration data based on the one or more voltage measurements, and outputting the calibration data to the catheter. According to one or more embodiments, the calibration engine 101 can be external to the console 160 and can be located, for example, in the catheter 110, in an external device, in a mobile device, in a cloud-based device, or can be a standalone processor. In this regard, the calibration engine 101 can be transferable/downloaded in electronic form, over a network.

In an example, the console 160 can be any computing device, as noted herein, including software (e.g., the calibration engine 101) and/or hardware (e.g., the processor 161 and the memory 162), such as a general-purpose computer, with suitable front end and interface circuits for transmitting and receiving signals to and from the probe 105, as well as for controlling the other components of the system 100. For example, the front end and interface circuits include input/output (I/O) communication interfaces that enables the console 160 to receive signals from and/or transfer signals to the at least one electrode 111. The console 160 can include real-time noise reduction circuitry typically configured as a field programmable gate array (FPGA), followed by an analog-to-digital (A/D) ECG or electrocardiograph/electromyogram (EMG) signal conversion integrated circuit. The console 160 can pass the signal from an A/D ECG or EMG circuit to another processor and/or can be programmed to perform one or more functions disclosed herein.

The display 165, which can be any electronic device for the visual presentation of the biometric data, is connected to the console 160. According to an exemplary embodiment, during a procedure, the console 160 can facilitate on the display 165 a presentation of a body part rendering to the physician 115 and store data representing the body part rendering in the memory 162. For instance, maps depicting motion characteristics can be rendered/constructed based on the trajectory information sampled at a sufficient number of points in the heart 120. As an example, the display 165 can include a touchscreen that can be configured to accept inputs from the medical professional 115, in addition to presenting the body part rendering.

In some embodiments, the physician 115 can manipulate the elements of the system 100 and/or the body part rendering using one or more input devices, such as a touch pad, a mouse, a keyboard, a gesture recognition apparatus, or the like. For example, an input device can be used to change a position of the catheter 110, such that rendering is updated. Note that the display 165 can be located at a same location or a remote location, such as a separate hospital or in separate healthcare provider networks.

According to one or more embodiments, the system 100 can also obtain the biometric data using ultrasound, computed tomography (CT), MRI, or other medical imaging techniques utilizing the catheter 110 or other medical equipment. For instance, the system 100 can obtain ECG data and/or anatomical and electrical measurements of the heart 120 (e.g., the biometric data) using one or more catheters 110 or other sensors. More particularly, the console 160 can be connected, by a cable, to BS electrodes, which include adhesive skin patches affixed to the patient 125. The BS electrodes can procure/generate the biometric data in the form of the BS ECG data. For instance, the processor 161 can determine position coordinates of the catheter 110 inside the body part (e.g., the heart 120) of the patient 125. The position coordinates may be based on impedances or electromagnetic fields measured between the BS electrodes and the electrode 111 of the catheter 110 or other electromagnetic components. Additionally, or alternatively, location pads, which generate magnetic fields used for navigation, may be located on a surface of the bed 130 and may be separate from the bed 130. The biometric data can be transmitted to the console 160 and stored in the memory 162. Alternatively, or in addition, the biometric data may be transmitted to a server, which may be local or remote, using a network as further described herein.

According to one or more exemplary embodiments, the catheter 110 may be configured to ablate tissue areas of a cardiac chamber of the heart 120. Inset 150 shows the catheter 110 in an enlarged view, inside a cardiac chamber of the heart 120. For instance, ablation electrodes, such as the at least one electrode 111, may be configured to provide energy to tissue areas of an intra-body organ (e.g., the heart 120). The energy may be thermal energy and may cause damage to the tissue area starting from the surface of the tissue area and extending into the thickness of the tissue area. The biometric data with respect to ablation procedures (e.g., ablation tissues, ablation locations, etc.) can be considered ablation data.

According to an example, with respect to obtaining the biometric data, a multi-electrode catheter (e.g., the catheter 110) can be advanced into a chamber of the heart 120. Anteroposterior (AP) and lateral fluorograms can be obtained to establish the position and orientation of each of the electrodes. ECGs can be recorded from each of the electrodes 111 in contact with a cardiac surface relative to a temporal reference, such as the onset of the P-wave in sinus rhythm from a BS ECG and/or signals from electrodes 111 of the catheter 110 placed in the coronary sinus. The system, as further disclosed herein, may differentiate between those electrodes that register electrical activity and those that do not due to absence of close proximity to the endocardial wall. After initial ECGs are recorded, the catheter may be repositioned, and fluorograms and ECGs may be recorded again. An electrical map (e.g., via cardiac mapping) can then be constructed from iterations of the process above.

Cardiac mapping can be implemented using one or more techniques. Generally, mapping of cardiac areas such as cardiac regions, tissue, veins, arteries and/or electrical pathways of the heart 120 may result in identifying problem areas such as scar tissue, arrhythmia sources (e.g., electric rotors), healthy areas, and the like. Cardiac areas may be mapped such that a visual rendering of the mapped cardiac areas is provided using a display, as further disclosed herein. Additionally, cardiac mapping (which is an example of heart imaging) may include mapping based on one or more modalities such as, but not limited to LAT, local activation velocity, an electrical activity, a topology, a bipolar mapping, a dominant frequency, or an impedance. Data (e.g., biometric data) corresponding to multiple modalities may be captured using a catheter (e.g., the catheter 110) inserted into a patient's body and may be provided for rendering at the same time or at different times based on corresponding settings and/or preferences of the physician 115.

As an example of a first technique, cardiac mapping may be implemented by sensing an electrical property of heart tissue, for example, LAT, as a function of the precise location within the heart 120. The corresponding data (e.g., biometric data) may be acquired with one or more catheters (e.g., the catheter 110) that are advanced into the heart 1120 and that have electrical and location sensors (e.g., the electrodes 111) in their distal tips. As specific examples, location and electrical activity may be initially measured on about 10 to about 20 points on the interior surface of the heart 120. These data points may be generally sufficient to generate a preliminary reconstruction or map of the cardiac surface to a satisfactory quality. The preliminary map may be combined with data taken at additional points to generate a more comprehensive map of the heart's electrical activity. In clinical settings, it is not uncommon to accumulate data at 100 or more sites (e.g., several thousand) to generate a detailed, comprehensive map of heart chamber electrical activity. The generated detailed map may then serve as the basis for deciding on a therapeutic course of action, for example, tissue ablation as described herein, to alter the propagation of the heart's electrical activity and to restore normal heart rhythm.

Further, cardiac mapping can be generated based on detection of intracardiac electrical potential fields (e.g., which is an example of IC ECG data and/or bipolar intracardiac reference signals). A non-contact technique to simultaneously acquire a large amount of cardiac electrical information may be implemented. For example, a catheter type having a distal end portion may be provided with a series of sensor electrodes distributed over its surface and connected to insulated electrical conductors for connection to signal sensing and processing means. The size and shape of the end portion may be such that the electrodes are spaced substantially away from the wall of the cardiac chamber. Intracardiac potential fields may be detected during a single cardiac beat. According to an example, the sensor electrodes may be distributed on a series of circumferences lying in planes spaced from each other. These planes may be perpendicular to the major axis of the end portion of the catheter. At least two additional electrodes may be provided adjacent at the ends of the major axis of the end portion. As a more specific example, the catheter may include four circumferences with eight electrodes spaced equiangularly on each circumference. Accordingly, in this specific implementation, the catheter may include at least 34 electrodes (32 circumferential and 2 end electrodes). As another more specific example, the catheter may include other multi-spline catheters, such as five soft flexible branches, eight radial splines, or a parallel splined pancake turner type (e.g., any of which may have a total of 42 electrodes).

As example of electrical or cardiac mapping, an electrophysiological cardiac mapping system and technique based on a non-contact and non-expanded multi-electrode catheter (e.g., the catheter 110) can be implemented. ECGs may be obtained with one or more catheters 110 having multiple electrodes (e.g., such as between 42 to 122 electrodes). According to this implementation, knowledge of the relative geometry of the probe and the endocardium can be obtained by an independent imaging modality, such as transesophageal echocardiography. After the independent imaging, non-contact electrodes may be used to measure cardiac surface potentials and construct maps therefrom (e.g., in some cases using bipolar intracardiac reference signals). This technique can include the following steps (after the independent imaging step): (a) measuring electrical potentials with a plurality of electrodes disposed on a probe positioned in the heart 120; (b) determining the geometric relationship of the probe surface and the endocardial surface and/or other reference; (c) generating a matrix of coefficients representing the geometric relationship of the probe surface and the endocardial surface; and (d) determining endocardial potentials based on the electrode potentials and the matrix of coefficients.

As another example of electrical or cardiac mapping, a technique and apparatus for mapping the electrical potential distribution of a heart chamber can be implemented. An intra-cardiac multi-electrode mapping catheter assembly can be inserted into the heart 120. The mapping catheter (e.g., the catheter 110) assembly can include a multi-electrode array with one or more integral reference electrodes (e.g., one or the electrodes 111) or a companion reference catheter. Examples of the mapping catheter include, but are not limited to, a single-axis sensor (SAS) catheter, dual-axis sensor (DAS), and a tri-axis sensor (TAS) catheter.

According to one or more exemplary embodiments, the electrodes may be deployed in the form of a substantially spherical array, which may be spatially referenced to a point on the endocardial surface by the reference electrode or by the reference catheter this is brought into contact with the endocardial surface. The preferred electrode array catheter may carry a number of individual electrode sites (e.g., at least 24). Additionally, this example technique may be implemented with knowledge of the location of each of the electrode sites on the array, as well as knowledge of the cardiac geometry. These locations are preferably determined by a technique of impedance plethysmography.

In view of electrical or cardiac mapping and according to another example, the catheter 110 can be a heart mapping catheter assembly that may include an electrode array defining a number of electrode sites. The heart mapping catheter assembly can also include a lumen to accept a reference catheter having a distal tip electrode assembly that may be used to probe the heart wall. The map heart mapping catheter assembly can include a braid of insulated wires (e.g., having 24 to 64 wires in the braid), and each of the wires may be used to form electrode sites. The heart mapping catheter assembly may be readily positionable in the heart 120 to be used to acquire electrical activity information from a first set of non-contact electrode sites and/or a second set of in-contact electrode sites.

Further, according to another example, the catheter 110 that can implement mapping electrophysiological activity within the heart can include a distal tip that is adapted for delivery of a stimulating pulse for pacing the heart or an ablative electrode for ablating tissue in contact with the tip. This catheter 110 can further include at least one pair of orthogonal electrodes to generate a difference signal indicative of the local cardiac electrical activity adjacent the orthogonal electrodes.

As noted herein, the system 100 can be utilized to detect, diagnose, and/or treat cardiac conditions. In example operation, a process for measuring electrophysiologic data in a heart chamber may be implemented by the system 100. The process may include, in part, positioning a set of active and passive electrodes into the heart 120, supplying current to the active electrodes, thereby generating an electric field in the heart chamber, and measuring the electric field at the passive electrode sites. The passive electrodes are contained in an array positioned on an inflatable balloon of a balloon catheter. In preferred embodiments, the array is said to have from 60 to 64 electrodes.

As another example operation, cardiac mapping may be implemented by the system 100 using one or more ultrasound transducers. The ultrasound transducers may be inserted into a patient's heart 120 and may collect a plurality of ultrasound slices (e.g., two dimensional or three-dimensional slices) at various locations and orientations within the heart 120. The location and orientation of a given ultrasound transducer may be known and the collected ultrasound slices may be stored such that they can be displayed at a later time. One or more ultrasound slices corresponding to the position of the probe 105 (e.g., a treatment catheter shown as catheter 110) at the later time may be displayed and the probe 105 may be overlaid onto the one or more ultrasound slices.

In view of the system 100, it is noted that cardiac arrhythmias, including atrial arrhythmias, may be of a multiwavelet reentrant type, characterized by multiple asynchronous loops of electrical impulses that are scattered about the atrial chamber and are often self-propagating (e.g., another example of the IC ECG data). Alternatively, or in addition to the multiwavelet reentrant type, cardiac arrhythmias may also have a focal origin, such as when an isolated region of tissue in an atrium fires autonomously in a rapid, repetitive fashion (e.g., another example of the IC ECG data). Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

For example, aFib occurs when the normal electrical impulses (e.g., another example of the IC ECG data) generated by the sinoatrial node are overwhelmed by disorganized electrical impulses (e.g., signal interference) that originate in the atria veins and PVs causing irregular impulses to be conducted to the ventricles. An irregular heartbeat results and may last from minutes to weeks, or even years. aFib is often a chronic condition that leads to a small increase in the risk of death often due to strokes. A line of treatment for aFib is medication that either slows the heart rate or revert the heart rhythm back to normal. Additionally, persons with aFib are often given anticoagulants to protect them from the risk of stroke. The use of such anticoagulants comes with its own risk of internal bleeding. In some patients, medication is not sufficient and their aFib is deemed to be drug-refractory, i.e., untreatable with standard pharmacological interventions. Synchronized electrical cardioversion may also be used to convert aFib to a normal heart rhythm. Alternatively, aFib patients are treated by catheter ablation.

A catheter ablation-based treatment may include mapping the electrical properties of heart tissue, especially the endocardium and the heart volume, and selectively ablating cardiac tissue by application of energy. Electrical or cardiac mapping (e.g., implemented by any electrophysiological cardiac mapping system and technique described herein) includes creating a map of electrical potentials (e.g., a voltage map) of the wave propagation along the heart tissue or a map of arrival times (e.g., a LAT map) to various tissue located points. Electrical or cardiac mapping (e.g., a cardiac map) may be used for detecting local heart tissue dysfunction. Ablations, such as those based on cardiac mapping, can cease or modify the propagation of unwanted electrical signals from one portion of the heart 120 to another.

The ablation process damages the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. Another example of an energy delivery technique includes irreversible electroporation (IRE), which provides high electric fields that damage cell membranes. In a two-step procedure (e.g., mapping followed by ablation) electrical activity at points within the heart 120 is typically sensed and measured by advancing the catheter 110 containing one or more electrical sensors (e.g., electrodes 111) into the heart 120 and obtaining/acquiring data at a multiplicity of points (e.g., as biometric data generally, or as ECG data specifically). This ECG data is then utilized to select the endocardial target areas, at which ablation is to be performed.

Cardiac ablation and other cardiac electrophysiological procedures have become increasingly complex as clinicians treat challenging conditions such as atrial fibrillation and ventricular tachycardia. The treatment of complex arrhythmias can now rely on the use of three-dimensional (3D) mapping systems to reconstruct the anatomy of the heart chamber of interest. In this regard, the calibration engine 101 employed by the system 100 herein manipulates and evaluates the biometric data generally, or the ECG data specifically, along with implements the online magnetic calibration algorithm, to produce improved tissue data that enables more accurate diagnosis, images, scans, and/or maps for treating an abnormal heartbeat or arrhythmia. For example, cardiologists rely upon software, such as the Complex Fractionated Atrial Electrograms (CFAE) module of the CARTO® 3 3D mapping system, produced by Biosense Webster, Inc. (Diamond Bar, Calif.), to generate and analyze ECG data. The calibration engine 101 of the system 100 enhances this software to generate and analyze the improved biometric data, which further provide multiple pieces of information regarding electrophysiological properties of the heart 120 (including the scar tissue) that represent cardiac substrates (anatomical and functional) of aFib.

Accordingly, the system 100 can implement a 3D mapping system, such as CARTO® 3 3D mapping system, to localize the potential arrhythmogenic substrate of the cardiomyopathy in terms of abnormal ECG detection. The substrate linked to these cardiac conditions is related to the presence of fragmented and prolonged ECGs in the endocardial and/or epicardial layers of the ventricular chambers (right and left). For instance, areas of low or medium voltage may exhibit ECG fragmentation and prolonged activities. Further, during sinus rhythm, areas of low or medium voltage may corresponds to a critical isthmus identified during sustained and organized ventricular arrhythmias (e.g., applies to non-tolerated ventricular tachycardias, as well as in the atria). In general, abnormal tissue is characterized by low-voltage ECGs. However, initial clinical experience in endo-epicardial mapping indicates that areas of low-voltage are not always present as the sole arrhythmogenic mechanism in such patients. In fact, areas of low or medium voltage may exhibit ECG fragmentation and prolonged activities during sinus rhythm, which corresponds to the critical isthmus identified during sustained and organized ventricular arrhythmias, e.g., applies only to non-tolerated ventricular tachycardias. Moreover, in many cases, ECG fragmentation and prolonged activities are observed in the regions showing a normal or near-normal voltage amplitude (>1-1.5 mV). Although the latter areas may be evaluated according to the voltage amplitude, they cannot be considered as normal according to the intracardiac signal, thus representing a true arrhythmogenic substrate. The 3D mapping may be able to localize the arrhythmogenic substrate on the endocardial and/or epicardial layer of the right/left ventricle, which may vary in distribution according to the extension of the main disease.

As another example operation, cardiac mapping may be implemented by the system 100 using one or more multiple-electrode catheters (e.g., the catheter 110). Multiple-electrode catheters are used to stimulate and map electrical activity in the heart 120 and to ablate sites of aberrant electrical activity. In use, the multiple-electrode catheter is inserted into a major vein or artery, e.g., femoral vein, and then guided into the chamber of the heart 120 of concern. A typical ablation procedure involves the insertion of the catheter 110 having at least one electrode 111 at its distal end, into a heart chamber. A reference electrode is provided, taped to the skin of the patient or by means of a second catheter that is positioned in or near the heart or selected from one or the other electrodes 111 of the catheter 110. Radio frequency (RF) current is applied to a tip electrode 111 of the ablating catheter 110, and current flows through the media that surrounds it (e.g., blood and tissue) toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the tip electrode 111 also occurs as a result of conduction from the heated tissue to the electrode itself. If the electrode temperature becomes sufficiently high, possibly above 60 degrees Celsius, a thin transparent coating of dehydrated blood protein can form on the surface of the electrode 111. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs, and the catheter 110 must be removed from the body and the tip electrode 111 cleaned.

Figure 2:
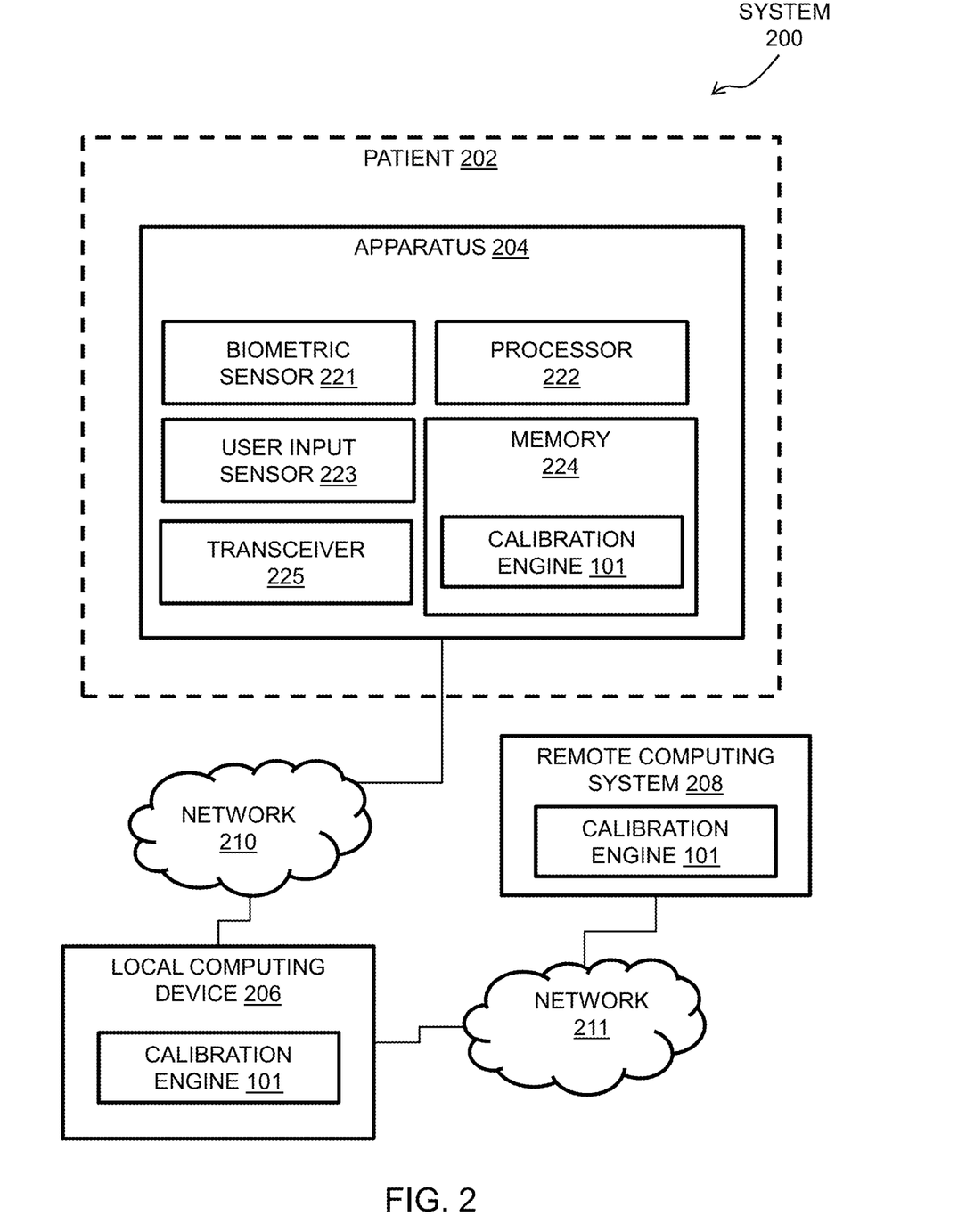
FIG. 2 illustrates a block diagram of an example system according to one or more embodiments.

Turning now to FIG. 2, a diagram of a system 200 in which one or more features of the disclosure subject matter can be implemented is illustrated according to one or more exemplary embodiments. The system 200 includes, in relation to a patient 202 (e.g., an example of the patient 125 of FIG. 1), an apparatus 204, a local computing device 206, a remote computing system 208, a first network 210, and a second network 211. Further, the apparatus 204 can include a biometric sensor 221 (e.g., an example of the catheter 110 of FIG. 1), a processor 222, a user input (UI) sensor 223, a memory 224, and a transceiver 225. Note that the calibration engine 101 of FIG. 1 is reused in FIG. 2 for ease of explanation and brevity.

According to an embodiment, the apparatus 204 can be an example of the system 100 of FIG. 1, where the apparatus 204 can include both components that are internal to the patient and components that are external to the patient. According to another embodiment, the apparatus 204 can be an apparatus that is external to the patient 202 that includes an attachable patch (e.g., that attaches to a patient's skin). According to another embodiment, the apparatus 204 can be internal to a body of the patient 202 (e.g., subcutaneously implantable), where the apparatus 204 can be inserted into the patient 202 via any applicable manner including orally injecting, surgical insertion via a vein or artery, an endoscopic procedure, or a laparoscopic procedure. According to an embodiment, while a single apparatus 204 is shown in FIG. 2, example systems may include a plurality of apparatuses.

Accordingly, the apparatus 204, the local computing device 206, and/or the remote computing system 208 can be programed to execute computer instructions with respect the calibration engine 101. As an example, the memory 223 stores these instructions for execution by the processor 222 so that the apparatus 204 can receive and process the biometric data via the biometric sensor 201. In this way, the processor 222 and the memory 223 are representative of processors and memories of the local computing device 206 and/or the remote computing system 208.

The apparatus 204, local computing device 206, and/or the remote computing system 208 can be any combination of software and/or hardware that individually or collectively store, execute, and implement the calibration engine 101 and functions thereof. Further, the apparatus 204, local computing device 206, and/or the remote computing system 208 can be an electronic, computer framework comprising and/or employing any number and combination of computing device and networks utilizing various communication technologies, as described herein. The apparatus 204, local computing device 206, and/or the remote computing system 208 can be easily scalable, extensible, and modular, with the ability to change to different services or reconfigure some features independently of others.

The networks 210 and 211 can be a wired network, a wireless network, or include one or more wired and wireless networks. According to an embodiment, the network 210 is an example of a short-range network (e.g., local area network (LAN), or personal area network (PAN)). Information can be sent, via the network 210, between the apparatus 204 and the local computing device 206 using any one of various short-range wireless communication protocols, such as Bluetooth, Wi-Fi, Zigbee, Z-Wave, near field communications (NFC), ultra-band, Zigbee, or infrared (IR). Further, the network 211 is an example of one or more of an Intranet, a local area network (LAN), a wide area network (WAN), a metropolitan area network (MAN), a direct connection or series of connections, a cellular telephone network, or any other network or medium capable of facilitating communication between the local computing device 206 and the remote computing system 208. Information can be sent, via the network 211, using any one of various long-range wireless communication protocols (e.g., TCP/IP, HTTP, 3G, 4G/LTE, or 5G/New Radio). Note that for either network 210 and 211 wired connections can be implemented using Ethernet, Universal Serial Bus (USB), RJ-11 or any other wired connection and wireless connections can be implemented using Wi-Fi, WiMAX, and Bluetooth, infrared, cellular networks, satellite or any other wireless connection methodology.

In operation, the apparatus 204 can continually or periodically obtain, monitor, store, process, and communicate via network 210 the biometric data associated with the patient 202. Further, the apparatus 204, local computing device 206, and/the remote computing system 208 are in communication through the networks 210 and 211 (e.g., the local computing device 206 can be configured as a gateway between the apparatus 204 and the remote computing system 208). For instance, the apparatus 204 can be an example of the system 100 of FIG. 1 configured to communicate with the local computing device 206 via the network 210. The local computing device 206 can be, for example, a stationary/standalone device, a base station, a desktop/laptop computer, a smart phone, a smartwatch, a tablet, or other device configured to communicate with other devices via networks 211 and 210. The remote computing system 208, implemented as a physical server on or connected to the network 211 or as a virtual server in a public cloud computing provider (e.g., Amazon Web Services (AWS)®) of the network 211, can be configured to communicate with the local computing device 206 via the network 211. Thus, the biometric data associated with the patient 202 can be communicated throughout the system 200.

Elements of the apparatus 204 are now described. The biometric sensor 221 may include, for example, one or more transducers configured to convert one or more environmental conditions into an electrical signal, such that different types of biometric data are observed/obtained/acquired. For example, the biometric sensor 221 can include one or more of an electrode (e.g., the electrode 111 of FIG. 1), a temperature sensor (e.g., thermocouple), a blood pressure sensor, a blood glucose sensor, a blood oxygen sensor, a pH sensor, an accelerometer, and a microphone.

The processor 222, in executing the calibration engine 101, can be configured to receive, process, and manage the biometric data acquired by the biometric sensor 221, and communicate the biometric data to the memory 224 for storage and/or across the network 210 via the transceiver 225. Biometric data from one or more other apparatuses 204 can also be received by the processor 222 through the transceiver 225. Also, as described in more detail herein, the processor 222 may be configured to respond selectively to different tapping patterns (e.g., a single tap or a double tap) received from the UI sensor 223, such that different tasks of a patch (e.g., acquisition, storing, or transmission of data) can be activated based on the detected pattern. In some embodiments, the processor 222 can generate audible feedback with respect to detecting a gesture.

The UI sensor 223 includes, for example, a piezoelectric sensor or a capacitive sensor configured to receive a user input, such as a tapping or touching. For example, the UI sensor 223 can be controlled to implement a capacitive coupling, in response to tapping or touching a surface of the apparatus 204 by the patient 202. Gesture recognition may be implemented via any one of various capacitive types, such as resistive capacitive, surface capacitive, projected capacitive, surface acoustic wave, piezoelectric and infrared touching. Capacitive sensors may be disposed at a small area or over a length of the surface, such that the tapping or touching of the surface activates the monitoring device.

The memory 224 is any non-transitory tangible media, such as magnetic, optical, or electronic memory (e.g., any suitable volatile and/or non-volatile memory, such as random-access memory or a hard disk drive). The memory 224 stores the computer instructions for execution by the processor 222.

The transceiver 225 may include a separate transmitter and a separate receiver. Alternatively, the transceiver 225 may include a transmitter and receiver integrated into a single device.

In operation, the apparatus 204, utilizing the calibration engine 101, observes/obtains the biometric data of the patient 202 via the biometric sensor 221, stores the biometric data in the memory, and shares this biometric data across the system 200 via the transceiver 225.

Figure 3:
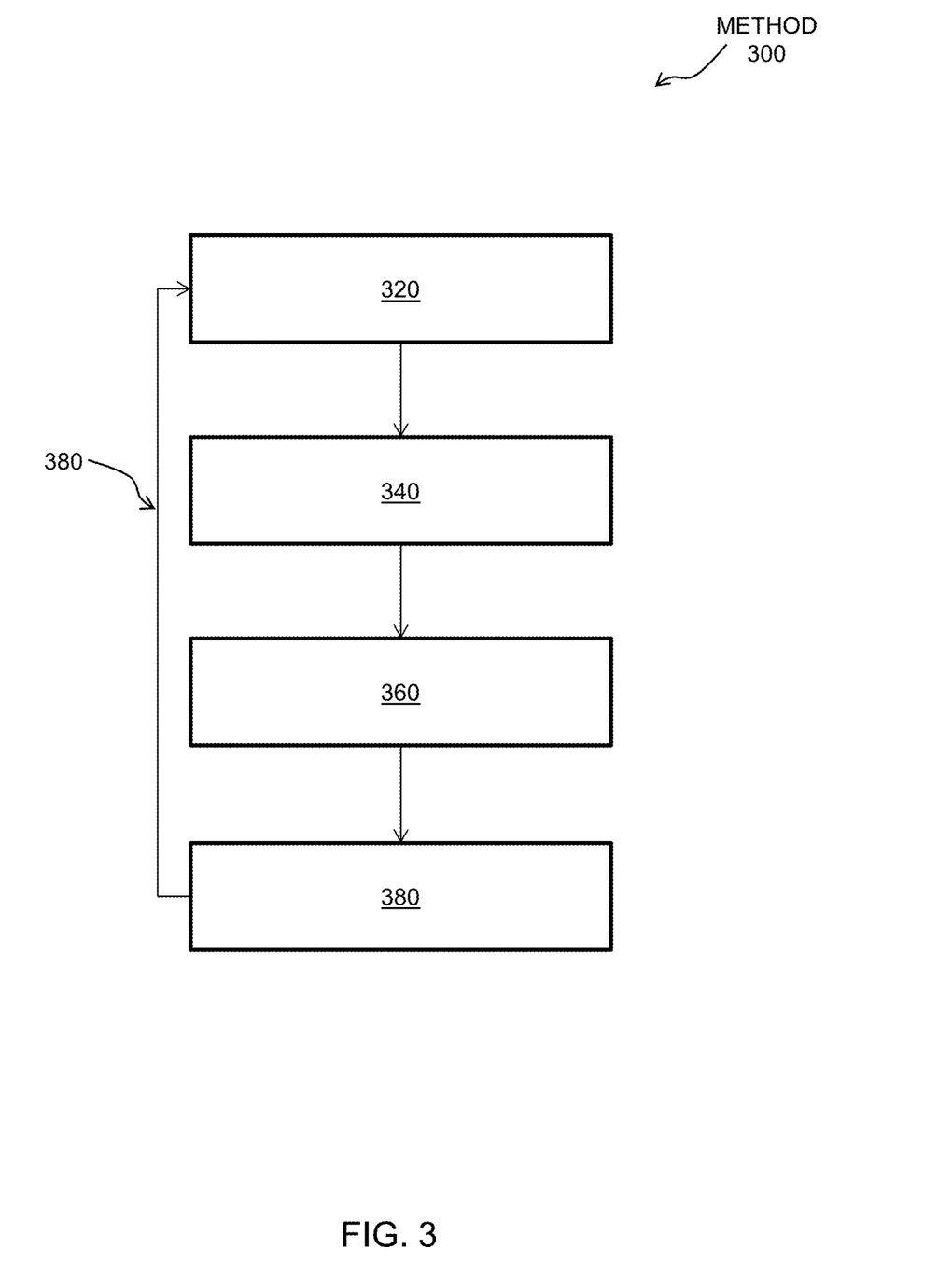
FIG. 3 illustrates an exemplary method according to one or more embodiments.

Turning now to FIG. 3, a method 300 (e.g., performed by the calibration engine 101 of FIG. 1 and/or of FIG. 2) is illustrated according to one or more exemplary embodiments. The method 300 addresses a need for on-site or in-the-field catheter calibration by producing an automatic calibration during navigation of the catheter 110 within the patient 125 (e.g., across a mapping volume) during a present clinical procedure.

The method begins at block 320, where the calibration engine 101 recalls first calibration data stored in a memory of the catheter 110 during usage (e.g., in the present clinical procedure). The first calibration data can be stored during catheter production or during the last calibration activity, which in either case is prior to the present clinical procedure.

Generally, calibration data includes one or more parameters, such as sensitivity and angle (e.g., directions). Sensitivity can be a coil sensitivity for each component of the catheter 110 (e.g., a sensitivity of each sensing coil regarding how much volts per gauss that sensing coil produces). Angle can be an angle between pairs of components of the catheter 110.

At block 340, the calibration engine 101 captures one or more voltage measurements from the catheter 110. Each of the one or more voltage measurements can be captured by one or more components of the catheter 110. More particularly, the one or more voltage measurements can be voltage readings taken by each of or a specific set of components (e.g., electrodes 111, sensors, or the like therein) of the catheter 110 at one or more points, as the catheter 110 is being navigated within the patient 125 (e.g., across a mapping volume). According to an embodiments, the one or more voltage measurements can originate from one or more transmitters. In this regard, the one or more voltage measurements are known to the system 100.

At block 360, the calibration engine 101 estimates second calibration data based on the one or more voltage measurements. According to one or more embodiments, the calibration engine 101 uses each voltage reading taken by each component to determine a real-time sensitivity and a real-time angle of the second calibration data.

At block 380, the calibration engine 101 outputs the second calibration data to the catheter 110, such that the second calibration data is applied to the catheter 110 (e.g., overwrites the first calibration data in the memory of the catheter 110). In this way, the first calibration data of block 320 can be modified by the second calibration data (e.g., the real-time sensitivity and the real-time angle) estimated in block 360.

At arrow 390, the method 300 loops. In this regard, the calibration engine 101 can repeat the method 300 to further refine or adjust any stored calibrations. That is, if any online calibration data (estimated at block 360) differ from stored calibration data (recalled at block 320), the calibration engine 101 can use the online calibration data to procure better performance from the catheter 110 (e.g., which may be functioning differently over time due to aging).

Figure 4:
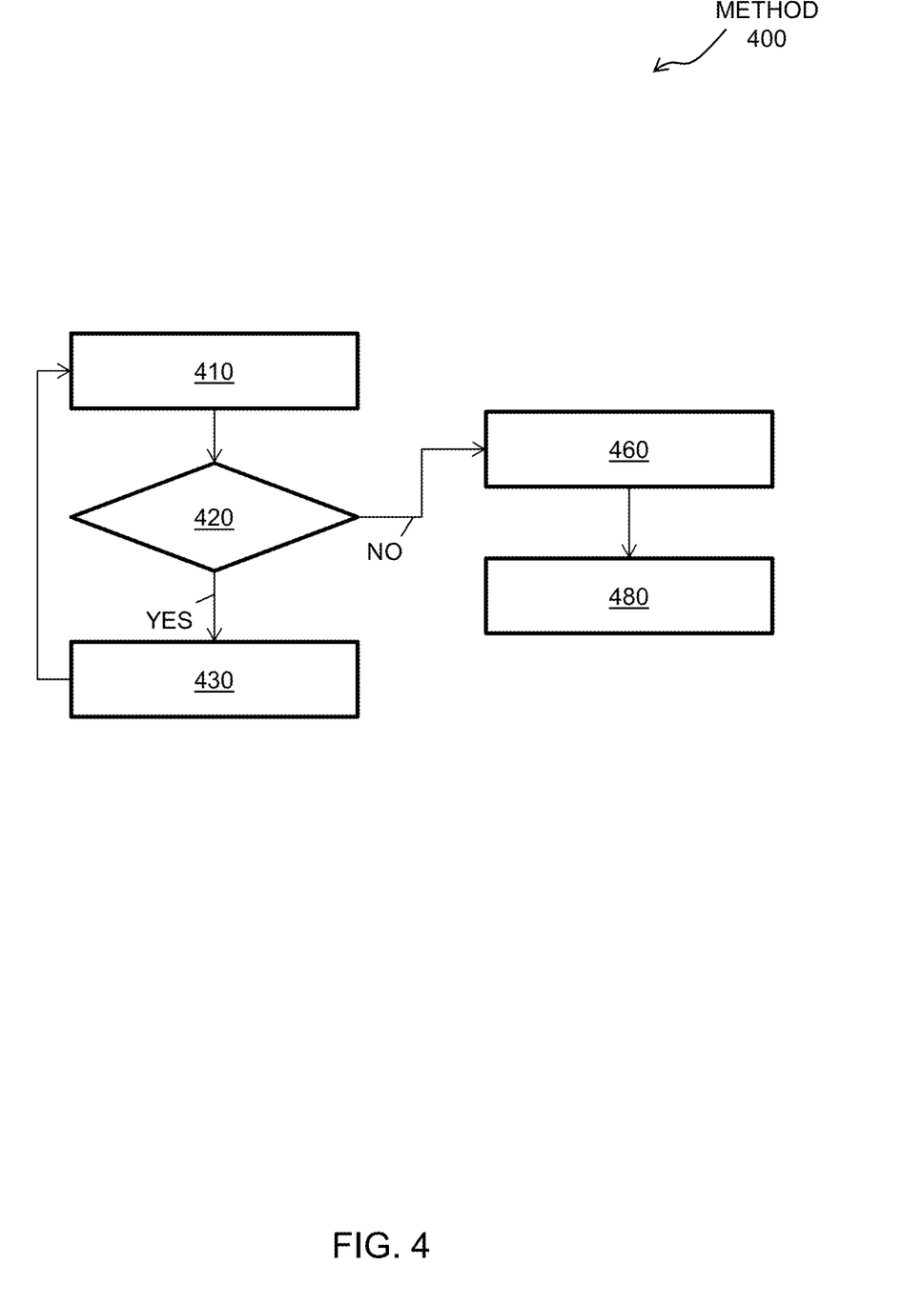
FIG. 4 illustrates an exemplary method according to one or more embodiments.

Turning now to FIG. 4, a method 400 (e.g., performed by the calibration engine 101 of FIG. 1 and/or of FIG. 2) is illustrated according to one or more exemplary embodiments. The method begins at block 410, where the calibration engine 101 captures one or more voltage measurements at a current position during a clinical procedure. According to one or more embodiments, the calibration engine 101 collects measurements (e.g., voltage readings) at sensing coils of the catheter 110 from one or more points in space (each current position as the catheter 110 advances), which may then be used by the calibration engine 101 to estimate the parameters In an exemplary embodiment, the system 100 can be or can be part of an electrophysiological system (e.g., the CARTO® system). Further, the catheter 110 can include a SAS sensor. The SAS sensor includes one axial sensor (a sensing coil) that has one calibration parameter (e.g., a coil sensitivity). Each sensing coil can collect a voltage measurement from each of the nine (in this implementation) transmitters at a single point. That is, a total number of measurements (T) is equal to a number transmitters calibrating (M) for each axial sensor (S) per point (X) (e.g., (M*S)*X=T). At maximum collection, the SAS sensor collects nine measurements at a single point (e.g., (9*1)*1=9).

Further, the catheter 110 can include a DAS sensor. The DAS sensor includes two axial sensors. The DAS sensor has three calibration parameters (e.g., two coil sensitivities and an angle therebetween). In a system with nine transmitters, the DAS sensor collects eighteen voltage measurements at a single point (e.g., (9*2)*1=18).

Furthermore, the catheter 110 can include a TAS sensor. The TAS sensor includes three axial sensors. The TAS sensor has six calibration parameters (e.g., three coil sensitivities and three angles between the pairs of coils). In turn, a total of twenty-seven voltage measurements (when nine transmitters are present) are captured at a single point (e.g., (9*3)*1=27).

At decision block 420, the calibration engine 101 determines if additional voltage measurements for calibration are required. If additional voltage measurements for calibration are required, the method 400 proceeds to block 430 (as shown by the YES arrow). The method 400 then proceeds through block 410 to decision block 420. If additional voltage measurements for calibration are not required, the method 400 proceeds to block 460 (as shown by the NO arrow).

To determine that additional voltage measurements are required, the catheter engine 101 may utilize a minimum threshold number related to a type of catheter being used and compare the minimum threshold number to number of the one or more voltage measurements captured. In this way, the calibration engine 110 and the system 100 can implement a rule that a number of voltage measurements is not less than a number of unknown parameters. In turn, a number of coils and/or transmitters drives the minimum threshold number.

According to one or more embodiments, the calibration engine 101 can calibrate SAS, DAS, and/or TAS sensors of the catheter 110. For calibrating the SAS sensor (i.e., one axial sensor), the minimum threshold number is six voltage measurements from six transmitters to guarantee that the calibration engine 101 has enough measurements to estimate the calibration data from a single point. For calibrating the DAS (i.e., two axial sensors), the minimum threshold number is ten voltage measurements from five transmitters (e.g., 10=5*2) to guarantee that the calibration engine 101 has enough measurements to estimate the calibration data from a single point. For calibrating the TAS sensor (i.e., three axial sensors), the minimum threshold number is twelve voltage measurements from four transmitters (e.g., 12=4*3) to guarantee that the calibration engine 101 has enough measurements to estimate the calibration data from a single point. If the calibration engine 110 and the system 100 collect from more than a single point, the minimum threshold number can be 4 transmitters for the DAS sensor and can be 3 transmitters for the TAS. Accordingly, one or more technical effects, advantages, and benefits the calibration engine 110 and the system 100 being adaptable into existing surgical/mapping systems to work with any catheter.

At block 430, the catheter 110 is advanced along a path to change the current position to a next position. Note that the catheter 110 can move between (e.g., predetermined) positions if the calibration engine 101 is calibrating on the path. According to an embodiment, the path can be roughly a size of an expected working volume (e.g., a sweep from one side of a heart chamber to another).

According to one or more embodiments, when the catheter 110 is navigated or advanced, additional points may be collected within a short amount of time. As shown in chart 500 of FIG. 5, if the catheter 110 is navigated and 10 points are collected, then 270 voltage measurements are taken. Similarly, if the catheter 110 is navigated and 100 points are collected, then 2700 voltage measurements are taken.

At block 460, the calibration engine 101 estimates calibration data (e.g., the at least twelve parameters) based on the one or more voltage measurements. Examples of parameters include, but are not limited to, position, orientation angles, sensitivity of each sensor, and mutual angle between each sensors.

According to one or more embodiments, the at least twelve parameters can include six location/orientation parameters and six calibration parameters for the TAS sensor. Note that the TAS sensor, generally, includes three coil sensitivities and three angles between pairs of coils (e.g., the six calibration parameters) as discussed herein.

Figure 5:
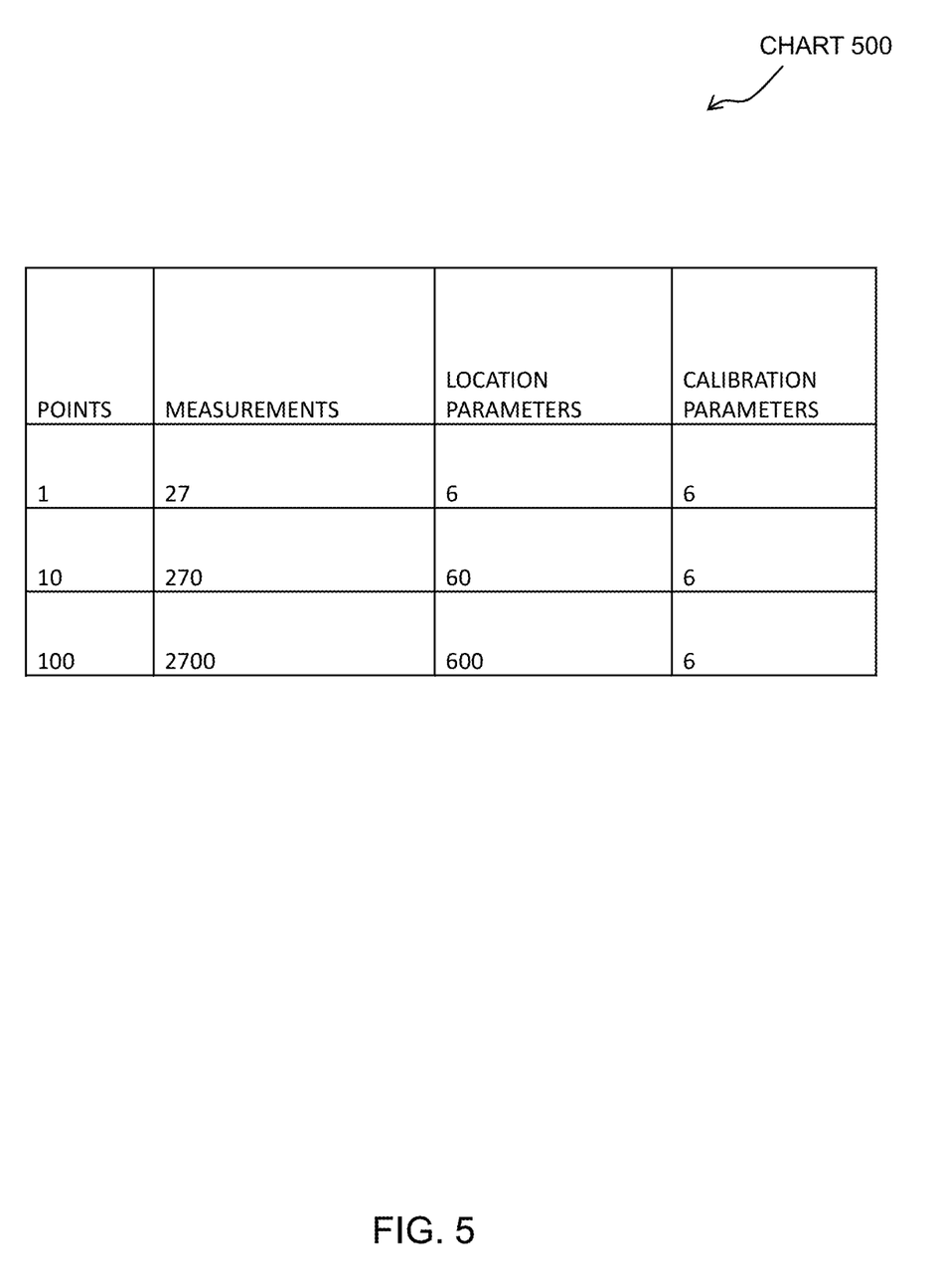
FIG. 5 illustrates a table according to one or more exemplary embodiments.

As shown in the chart 500 of FIG. 5, if 270 voltage measurements are taken, then sixty location/orientation parameters and six calibration parameters can be estimated (e.g., 66 parameters). Similarly, if 2700 voltage measurements are taken, then 600 location/orientation parameters and six calibration parameters can be estimated (e.g., 606 parameters). Note that each of the location/orientation parameter relies on the TAS position, and thus the number of location/orientation parameters increases to correspond to the number of positions (from blocks 410 and 420). Note also that each of the calibration parameters do not depend on the TAS position, and thus the number of calibration parameters remains at six. One or more advantages, technical effects, and/or benefits of the calibration engine 101 and the online magnetic calibration system includes the ability to estimate the calibration data from several points across a mapping volume, because then the estimations are more robust with respect to local field distortions.

For example, for the TAS sensor, it is noted that a total of 27 measurements are taken at 1 point. It is further noted that, as more points are collected to increase a number of measurements, catheter calibration improves (e.g., the more measurements that are taken during a procedure, the more robust an estimation will be for the calibration data). As shown in the chart 500, with 10 points, 270 measurements may be used to estimate 66 parameters out of which 6 are the calibration parameters. With 100 points, 2700 measurements may be used to estimate 606 parameters (again, out of which 6 are the calibration parameters). The estimated calibration parameters may then be combined with the previously known geometric relations between the sensor and the catheter, which ultimately provides the location and orientation of the catheter during the navigation procedure. So the resultant location may be as accurate, if not better than the calibration provided by the current calibration chamber.

At block 480, the calibration engine 101 applies the calibration data to the catheter 110. Also, according to one or more embodiments, the estimated calibration parameters can be then combined with known, prior relations between the sensors and the catheter 110. For example, a TAS sensor is aligned with the shaft 112.

According to one or more embodiments, the calibration engine 101 within a magnetic location system utilizes a mathematical model (e.g., a set of formulas) that intake a number of inputs. The number of inputs can include, but are not limited to, a magnetic field model (e.g., the magnetic field values at each point in the mapping volume), the calibration data as described herein, a sensor position and orientation in a mapping volume. The model outputs are the predictions of voltage values produced by each sensing coil. When the calibration engine 101 is operating in a normal mode, the magnetic field is known as it is stored in a memory of a field generator, the calibration data is known as it is stored in the catheter memory, and the sensor position and orientation are estimated by finding the position and orientation values so that model predicted voltages best match the actual measured voltages. When the calibration engine 101 is operating in a calibration mode, the magnetic field is known as it is stored in a memory of a field generator, while the calibration data and the sensor position and orientation are estimated by finding calibration data values and position and orientation values so that the model predicted voltages best match the actual measured voltages. Further, in calibration mode, a location estimation does not need to be as robust as in normal mode (because the calibration engine 101 has more parameters to estimate). Yet, using many points, the calibration engine 101 can robustly estimate the calibration data (e.g., as it does not depend on chosen points). Note that the calibration engine 101 can start in the calibration mode until the calibration data is estimated and can switch to the normal mode (e.g., using any estimated calibration data instead of the stored one).

Additionally, the calibration engine 101 can utilize the calibration data to determine a life cycle of the catheter 110, along with a degradation of the electrodes/coils from previous calibrations. For instance, the calibration engine 101 can set and check a threshold on a difference between stored and online-estimated calibration parameters to prevent usage (e.g., by deactivating the catheter 110) if the catheter 110 is a too degraded (e.g., greater than the threshold). As the catheter 110 may still be usable (e.g., despite being beyond the threshold), the calibration engine 101 and the system 100 can provide notifications to the physician 115 (or a medical professional or clinician) in accordance with the threshold and the physician 115 can decide to use the catheter 110 anyway (e.g., based on their knowledge that use is not too risky).

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for performing an online magnetic calibration of a catheter that improves accuracy of a map of a portion of a body of a patient generated during a medical procedure, the method comprising:
   capturing one or more voltage measurements by one or more components of the catheter while the catheter is within the patient during the medical procedure;
   estimating calibration data by comparing the one or more voltage measurements with previously stored calibration data; and
   automatically adjusting one or more parameters of the catheter based on the calibration data while the catheter is within the patient during the medical procedure, wherein the one or more parameters of the catheter are subsequently utilized during the medical procedure to generate the map of the portion of the body of the patient.

2. The method of claim 1, wherein the one or more voltage measurements comprise voltage readings taken by each or a specific set of the one or more components.

3. The method of claim 1, wherein the one or more parameters include a sensitivity and angle.

4. The method of claim 3, wherein the sensitivity comprises a coil sensitivity for each of the one or more components of the catheter.

5. The method of claim 3, wherein the angle comprises an angle between at least one pair of the one or more components of the catheter.

6. The method of claim 1, wherein the one or more components comprise at least one axial sensor.

7. The method of claim 6, wherein the one or more voltage measurements by the at least one axial sensor are from at least three transmitters.

8. The method of claim 1, wherein the catheter comprises at least one of a single-axis sensor, a dual-axis sensor, or a tri-axis sensor.

9. The method of claim 1, wherein the calibration data comprises location/orientation and calibration parameters.

10. The method of claim 1, wherein a number of the one or more voltage measurements used in the estimating is determined based on a location of the catheter within the patient.

11. A system for performing an online magnetic calibration of a catheter that improves accuracy of a map of a portion of a body of a patient generated by the catheter during a medical procedure, the system comprising:
    a memory storing processor executable code;
    a communication interface communicatively coupled to the catheter; and
    one or more processors communicatively coupled to the memory and the communication interface, wherein the one or more processors are collectively configured to:
    capture one or more voltage measurements by one or more components of the catheter while the catheter is within the patient during the medical procedure,
    estimate calibration data by comparing the one or more voltage measurements with previously stored calibration data, and
    automatically adjust one or more parameters of the catheter based on the calibration data while the catheter is within the patient during the medical procedure, wherein the one or more parameters of the catheter are subsequently utilized during the medical procedure to generate the map of the portion of the body of the patient.

12. The system of claim 11, wherein the one or more voltage measurements comprise voltage readings taken by each or a specific set of the one or more components.

13. The system of claim 11, wherein the one or more parameters include a sensitivity and angle.

14. The system of claim 13, wherein the sensitivity comprises a coil sensitivity for each of the one or more components of the catheter.

15. The system of claim 13, wherein the angle comprises an angle between at least one pair of the one or more components of the catheter.

16. The system of claim 11, wherein the one or more components comprise at least one axial sensor.

17. The system of claim 16, wherein the one or more voltage measurements by the at least one axial sensor are from at least three transmitters.

18. The system of claim 11, wherein the catheter comprises at least one of a single-axis sensor, a dual-axis sensor, or a tri-axis sensor.

19. The system of claim 11, wherein the calibration data comprises location/orientation and calibration parameters.

20. A non-transitory computer readable storage medium storing instructions for performing an online magnetic calibration of a catheter, the instructions when executed by one or more processors cause the one or more processors to collectively execute a method comprising:
    capturing, one or more voltage measurements by one or more components of the catheter while the catheter is within a patient during a medical procedure;
    estimating calibration data by comparing the one or more voltage measurements with previously stored calibration data; and
    automatically adjusting one or more parameters of the catheter based on the calibration data while the catheter is within the patient during the medical procedure, wherein the one or more parameters of the catheter are subsequently utilized during the procedure to map a portion of a body of the patient.

* * * * *

UNITED STATES PATENT AND TRADEMARK OFFICE
CERTIFICATE OF CORRECTION

PATENT NO. : 12,059,535 B2
APPLICATION NO. : 17/161015
DATED : August 13, 2024
INVENTOR(S) : Daniel Osadchy et al.

Page 1 of 1

It is certified that error appears in the above-identified patent and that said Letters Patent is hereby corrected as shown below:

On the Title Page

1. In Item (57), under "ABSTRACT", in Column 2, Line 2, delete "executed" and insert -- is executed --, therefor.

In the Specification

2. In Column 1, Line 34, delete "executed" and insert -- is executed --, therefor.
3. In Column 2, Line 7, delete "can a" and insert -- can be a --, therefor.
4. In Column 4, Line 15, delete "used are" and insert -- are used --, therefor.
5. In Column 4, Line 47, delete "diagnosis, and treatment" and insert -- diagnose, and treat --, therefor.
6. In Column 5, Line 7, delete "and or" and insert -- and/or --, therefor.
7. In Column 5, Line 53, delete "respect the" and insert -- respect to the --, therefor.
8. In Column 6, Line 36, delete "touch pad," and insert -- touchpad, --, therefor.
9. In Column 10, Line 47, delete "radiofrequency" and insert -- radio frequency --, therefor.
10. In Column 11, Line 2, delete "implements" and insert -- implementing --, therefor.
11. In Column 11, Line 8, delete "3 3D" and insert -- 3D --, therefor.
12. In Column 11, Line 18, delete "3 3D" and insert -- 3D --, therefor.
13. In Column 12, Line 52, delete "programed" and insert -- programmed --, therefor.
14. In Column 12, Line 52, delete "respect the" and insert -- respect to the --, therefor.
15. In Column 13, Line 37, delete "and/the" and insert -- and/or the --, therefor.
16. In Column 15, Line 42, delete "parameters" and insert -- parameters. --, therefor.
17. In Column 15, Line 51, delete "number" and insert -- number of --, therefor.
18. In Column 16, Line 39, delete "benefits the" and insert -- benefits of the --, therefor.
19. In Column 18, Line 13, delete "a too" and insert -- too --, therefor.
20. In Column 18, Line 55, delete "wire" and insert -- wire, --, therefor.
21. In Column 19, Line 13, delete "one more" and insert -- one or more --, therefor.

Signed and Sealed this
Thirty-first Day of December, 2024

Derrick Brent
*Acting Director of the United States Patent and Trademark Office*